US006815558B1

(12) United States Patent
Weferling

(10) Patent No.: US 6,815,558 B1
(45) Date of Patent: *Nov. 9, 2004

(54) PROCESS FOR PREPARING (METAL) ALKYLPHOSPHONITES II

(75) Inventor: Norbert Weferling, Hürth (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,420

(22) Filed: May 25, 2000

(30) Foreign Application Priority Data

May 25, 1999 (DE) .......................................... 199 23 743

(51) Int. Cl.$^7$ .............................. C07F 9/28; C07F 9/32; C07F 9/22

(52) U.S. Cl. ............................ 562/8; 558/89; 558/104; 568/8; 524/133

(58) Field of Search ............................... 562/8; 558/89, 558/104; 568/8; 524/133

(56) References Cited

U.S. PATENT DOCUMENTS

| | | | |
|---|---|---|---|
| 2,724,718 A | | 11/1955 | Stiles et al. |
| 3,316,293 A | * | 4/1967 | Carr et al. ...................... 562/8 |
| 3,579,576 A | * | 5/1971 | Angstadt .................... 562/816 |
| 4,379,132 A | | 4/1983 | Annarelli et al. ........... 423/305 |
| 5,973,194 A | * | 10/1999 | Weferling et al. ............. 562/8 |
| 6,011,172 A | * | 1/2000 | Weferling et al. ............. 562/8 |
| 6,090,967 A | * | 7/2000 | Horold et al. .............. 558/105 |
| 6,090,968 A | * | 7/2000 | Horold et al. .............. 558/137 |
| 6,232,493 B1 | * | 5/2001 | Weferling et al. ............. 562/8 |
| 6,242,642 B1 | * | 6/2001 | Weferling et al. ............. 562/8 |
| 6,278,012 B1 | * | 8/2001 | Horold et al. .............. 558/110 |
| 6,300,516 B1 | * | 10/2001 | Weferling et al. ............. 562/8 |
| 6,329,544 B1 | * | 12/2001 | Weferling et al. ............. 562/8 |
| 6,355,832 B1 | * | 3/2002 | Weferling et al. ............. 562/8 |
| 6,359,171 B1 | * | 3/2002 | Weferling et al. ............. 562/8 |
| 6,420,598 B1 | * | 7/2002 | Weferling et al. ............. 562/8 |
| 6,583,315 B2 | * | 6/2003 | Sicken et al. ................ 562/20 |

FOREIGN PATENT DOCUMENTS

| | | |
|---|---|---|
| DE | 875 045 | 11/1955 |
| WO | WO 99/28326 | 6/1999 |

OTHER PUBLICATIONS

Trofimov, Boris, et al., Phosphorus, Sulfur and Silicon, 1996, vols. 109–110, pp 601–604, Generation of Phosphide Anions from Phosphorus Red and Phosphine in Strongly Basic Systems to Form Organylphoshines and –Oxides, Overseas Publishers Association.

Trofimov, B.A., et al., Phosphorus, Sulfur and Silicon, 1991, vol. 55, pp 271–274, Superbase–Induced Generation of Phosphide and Phosphinite Ions as Applied in Organic Synthesis, Gordon and Breach Science Publishers S.A.

Semenzin, Delphine, et al., Tetrahedron Letters, 1994, vol. 35, No. 20, pp 3297–3300, Alkylation of Phosphine PH3 Generated from Red Phosphorus, Elsevier Science Ltd.

* cited by examiner

Primary Examiner—Joseph D. Anthony
(74) Attorney, Agent, or Firm—Anthony A. Bisulca

(57) ABSTRACT

The invention relates to a process for the preparation of (metal) salts of alkylphosphonous acids, which comprises reacting elemental yellow phosphorus with alkyl halides in the presence of carbonates, bicarbonates, amides, alkoxides, amine bases and/or solid hydroxides as bases.

The invention also relates to the use of the (metal) salts of alkylphosphonous acids prepared by this process.

13 Claims, No Drawings

PROCESS FOR PREPARING (METAL) ALKYLPHOSPHONITES II

BACKGROUND OF THE INVENTION

The invention relates to a process for the preparation of (metal) salts of alkylphosphonous acids, and to the use of the (metal) salts of alkylphosphonous acids prepared by this process.

Organic phosphorus compounds are increasing in industrial importance. They are employed principally for the preparation of herbicides or as herbicides themselves, as extractants and as flame retardants. The starting materials used are preferably $PH_3$ and phosphorus halides, which must themselves in turn be prepared from yellow phosphorus.

The reaction of red phosphorus in the superbasic medium dimethyl sulfoxide/potassium hydroxide (DMSO/KOH) with acetylenes or olefins as alkylating agent (Trofimov et al., Phosphorus, Sulfur and Silicon 55, 271, 1991) preferentially gives triorganylphosphines and triorganylphosphine oxides.

The alkylation of red phosphorus using acrylonitrile under the abovementioned conditions with ultrasound treatment of the reaction mixture gives predominantly secondary phosphine oxide. If 1,1-diphenylethylene is employed, tert-phosphine oxide (30%), sec-phosphine oxide (10%) and phosphinic acid (35%) are obtained [D. Semenzin et al., Tetrahedron Letters 35, 3297, 1994].

It has also been attempted (Trofimov et al., Main Group Chem. News 4, 18, 1996, Phosphorus, Sulfur and Silicon, 109/110, 601, 1996) to react elemental phosphorus in its red modification with alkyl halides in the presence of potassium hydroxide, water, dioxane and a phase-transfer catalyst. The main product found comprised tert-phosphine oxides (up to 75% in the case of benzyl bromide, about 60–65% in the case of butyl bromide). As byproducts, sec-phosphine oxides and phosphinic acid esters are obtained with 19% and 6% respectively, but the former only in the presence of zinc powder as reducing agent.

However, the abovementioned processes have the disadvantage that first of all the red phosphorus or organophosphorus intermediates have to be prepared. The processes are technically very complex and consequently also not economical, and the products obtained often have to be purified subsequently at great effort. In particular, the specific preparation of certain compounds in high yield is frequently particularly difficult.

In addition, a number of starting materials, such as halogen-containing phosphorus compounds or phosphines, are unsuitable from the very beginning for a large-scale and economical process owing to their environmental toxicity.

SUMMARY OF THE INVENTION

There is therefore a demand for a process for the preparation of (metal) salts of alkylphosphonous acids which can be carried out in a simple manner and in which uniform products are obtained in high yield. A process of this type should also be clearly superior to those known hitherto in economic and environmental terms.

The invention therefore has the object of providing a process for the preparation of (metal) salts of alkylphosphonous acids which avoids the abovementioned disadvantages and with which the desired end products can be prepared without difficulty.

DESCRIPTION OF THE PREFERRED EMBODIMENTS

This object is achieved by a process of the type described at the outset, which comprises reacting elemental yellow phosphorus with alkyl halides in the presence of carbonates, bicarbonates, amides, alkoxides, amine bases and/or solid hydroxides as bases.

The reaction is preferably carried out in a two-phase system comprising at least one base and an organic solvent.

The alkyl halides employed are preferably methyl chloride or methyl bromide.

The organic solvents employed are preferably straight-chain or branched alkanes, alkyl-substituted aromatic solvents, water-immiscible or only partially water-miscible alcohols or ethers, alone or in combination with one another.

The organic solvent employed is particularly preferably toluene, alone or in combination with alcohols.

The reaction is preferably carried out in the presence of a phase-transfer catalyst.

The phase-transfer catalyst is preferably a tetraalkylphosphonium halide, triphenylalkylphosphonium halide or tetraorganylammonium halide.

The temperature in the reaction is preferably from −20 to +60° C.

The temperature is particularly preferably from 0 to 30° C.

The reaction is preferably carried out under a pressure of from 0 to 10 bar.

The process according to the invention is preferably carried out by suspending or dissolving the yellow phosphorus in a solvent or solvent mixture and then reacting it with an alkyl halide and at least one base.

The yellow phosphorus and the alkyl halide are preferably reacted with one another in a molar ratio of from 1:1 to 1:3, where the molar ratio of yellow phosphorus to base is from 1:1 to 1:5.

The two-phase system obtained after the reaction is preferably separated and processed further as an aqueous phase.

The invention also relates to the use of the (metal) salts of alkylphosphonous acids prepared in accordance with the invention as precursors for chemical syntheses.

The invention also relates to the use of the (metal) salts of alkylphosphonous acids prepared in accordance with the invention for the preparation of organophosphorus compounds.

The invention also relates to the use of the (metal) salts of alkylphosphonous acids prepared in accordance with the invention as flame retardants or for the preparation of flame retardants.

The invention relates in particular to the use of the (metal) salts of alkylphosphonous acids prepared in accordance with the invention for the preparation of flame retardants for thermoplastic polymers, such as polyethylene terephthalate, polybutylene terephthalate or polyamide.

The invention relates in particular to the use of the (metal) salts of alkylphosphonous acids prepared in accordance with the invention for the preparation of flame retardants for thermosetting resins, such as unsaturated polyester resins, epoxy resins, polyurethanes or acrylates.

Surprisingly, it has been found that elemental yellow phosphorus can be reacted with alkylating agents in a two-phase system (organic solvent/base) and, if desired, in the presence of a (phase-transfer) catalyst under extremely mild conditions by the process according to the invention to give the (metal) salts of the corresponding alkylphosphonous acid RP(:O)HOH.

In addition, small amounts of dialkylphosphinic acids, trialkylphosphine oxide $R_3P(:O)$, dialkylphosphine oxide and unidentified phosphorus compounds may be formed; these can be removed from the product mixture in the usual manner. A further byproduct formed is hydrogen, which can easily be separated off from the reaction mixture. The abovementioned dialkylphosphinic acids can be separated off from the reaction mixture and employed or further processed elsewhere.

Surprisingly, the process according to the invention gives neither phosphine ($PH_3$) nor alkylphosphines ($RPH_2$, $R_2PH$) in significant amounts. Through the choice of suitable reaction conditions—such as the addition of small amounts of alcohols to the organic phase—the formation of all unidentified phosphorus-containing byproducts can be minimized to a surprisingly low content of a few mol % of the yellow phosphorus employed, in favor of the main product, the (metal) salts of alkylphosphonous acid.

The process according to the invention can be carried out, for example, by introducing the solvent together with the phase-transfer catalyst and warming the mixture to above the melting point of the yellow phosphorus, then adding the elemental (yellow) phosphorus, cooling the mixture to temperatures of, for example, from −10 to +30° C. with vigorous stirring, and subsequently adding the alkyl halide.

The reaction is initiated by addition of the base. When the reaction is complete, the reaction mixture can be diluted, for example with water, and the readily volatile components ($H_2$, $PH_3$, $RPH_2$, $R_2PH$ and excess alkyl halide, etc.) are subsequently removed.

This process gives a base-containing/organic two-phase system whose phases are separated. The contents from the phases are determined analytically.

The base-containing phase can be worked up by the known methods of the prior art in order to obtain the pure acids, such as, for example, alkylphosphonous acid (for example by ion exchange or distillation).

The reactants can also be combined in a different sequence, for example by introducing them continuously into a reactor (pressure tube, pressure reactor or cascade) in the above-defined molar ratio and removing them from the reactor again after a residence time of from 0.5 to 2 hours. The organic phase obtained after the phase separation, which still contains the majority of any phase-transfer catalyst employed, is advantageously recycled.

EXAMPLES

Example 1
Methylphosphonous Acid

A solution of 26.1 g (0.05 mol) of tributylhexadecylphosphonium bromide in 1000 ml of toluene was introduced into a 5 l stainless-steel pressure reactor and pre-heated to 60° C. 31 g (1 mol) of yellow phosphorus were added, the mixture was cooled to −10° C. with vigorous stirring, and 202 g (4 mol) of methyl chloride were then metered in. The mixture was then warmed to 20° C., and 500 g of 50% aqueous potassium carbonate solution were metered in over the course of 8 hours, during which the temperature was held at 20° C. Over the course of a further hour, 300 g of water were added, the mixture was then stirred for a further two hours, and the reactor was subsequently decompressed via combustion. Two homogeneous liquid phases were obtained, which were separated and analyzed.

The aqueous phase (weight: 900 g) contained 52.7 mol % of methylphosphonous acid, 18.9 mol % of phosphorous acid, 22.7 mol % of hypophosphorous acid, 2.8 mol % of dimethylphosphinic acid in the form of their potassium salts and 2 mol % of dimethyldiphosphine.

The acids can be obtained from the salts prepared in example 1 in a known manner, for example by ion exchange.

What is claimed is:

1. A process for the preparation of (metal) salts of alkylphosphonous acids, which comprises reacting elemental yellow phosphorus with alkyl halides in the presence of carbonates, bicarbonates, amides, alkoxides, amine bases and/or solid hydroxides as bases.

2. A process as claimed in claim 1, wherein the alkyl halides employed are methyl chloride or methyl bromide.

3. A process as claimed in claim 1, wherein the temperature during the reaction is from −20 to +60° C.

4. A process as claimed in claim 1, wherein the temperature is from 0 to 30° C.

5. A process as claimed in claim 1, wherein the reaction is carried out at a pressure of from 0 to 10 bar.

6. A process as claimed in claim 1, wherein the yellow phosphorus is suspended or dissolved in a solvent or solvent mixture and then reacted with an alkyl halide and at least one base.

7. A process as claimed in claim 1, wherein the yellow phosphorus and the alkyl halide are reacted in a molar ratio of from 1:1 to 1:3, where the molar ratio of yellow phosphorus to base is from 1:1 to 1:5.

8. A process as claimed in claim 1, wherein the reaction is carried out in the presence of a phase-transfer catalyst.

9. A process as claimed in claim 8, wherein the phase-transfer catalyst is a tetraalkylphosphonium halide, triphenylalkylphosphonium halide or tetraorganylammonium halide.

10. A process as claimed in claim 1, wherein the reaction is carried out in a two-phase system comprising at least one base and an organic solvent.

11. A process as claimed in claim 1, wherein the organic solvents employed are straight-chain or branched alkanes, alkyl-substituted aromatic solvents, water-immiscible or only partially water-miscible alcohols or ethers, alone or in combination with one another.

12. A process as claimed in claim 1, wherein the organic solvent employed is toluene, alone or in combination with alcohols.

13. A process as claimed in claim 1, wherein the two-phase system obtained after the reaction is separated and further processed.

* * * * *

UNITED STATES PATENT AND TRADEMARK OFFICE
CERTIFICATE OF CORRECTION

PATENT NO. : 6,815,558 B1
DATED : November 9, 2004
INVENTOR(S) : Norbert Weferling and Martin Sicken It is certified that error appears in the above-identified patent and that said Letters Patent is hereby corrected as shown below:

Title page,
Item [75], should read:
-- [75] Inventors, Norbert Weferling, Hürth (DE) and Martin Sicken, Köln, (DE) --.

Signed and Sealed this

Twenty-seventh Day of December, 2005

JON W. DUDAS
*Director of the United States Patent and Trademark Office*